(12) United States Patent
Liao et al.

(10) Patent No.: US 7,335,361 B2
(45) Date of Patent: Feb. 26, 2008

(54) FUSION ANTIGEN USED AS VACCINE

(75) Inventors: Chao-Wei Liao, Chunan Town (TW);
Chung-Nan Weng, Chunan Town (TW)

(73) Assignee: Animal Technology Institute Taiwan (TW)

( * ) Notice: Subject to any disclaimer, the term of this patent is extended or adjusted under 35 U.S.C. 154(b) by 490 days.

(21) Appl. No.: 10/457,574

(22) Filed: Jun. 9, 2003

(65) Prior Publication Data

US 2004/0247617 A1  Dec. 9, 2004

(51) Int. Cl.
*A61K 39/00* (2006.01)
*A61K 39/155* (2006.01)

(52) U.S. Cl. .............................. 424/192.1; 424/211.1; 435/5

(58) Field of Classification Search ............ None
See application file for complete search history.

(56) References Cited

U.S. PATENT DOCUMENTS

| 5,458,878 | A | 10/1995 | Pastan et al. | 424/260.1 |
|---|---|---|---|---|
| 5,705,163 | A | 1/1998 | Pastan et al. | 424/260.1 |
| 5,854,044 | A | 12/1998 | Pastan et al. | 435/194 |
| 6,437,095 | B1 | 8/2002 | Lilie et al. | 530/345 |

FOREIGN PATENT DOCUMENTS

WO    WO 98/50426 A1 * 11/1998

OTHER PUBLICATIONS

C.W. Liao, et al; A Target-Specific Chimeric Toxin Composed . . . Domain; Appl Microbiol Biotechnol; (1995); 43: 498-507.
Constantin A. Bona, et al; Towards Development of T-Cell Vaccines; Review Immunology Today; vol. 19; No. 3; Mar. 1998; p. 126-132.
J. Plana-Duran, et al; New Strategies in the Development of . . . Coronaviruses; Vet. Res. 31 (2000); p. 41-42.
J.N. Samsom, et al; Direct Cytolytic Activity of PBMC . . . Syndrome; Vet. Res. 31 (2000); p. 44.
Anette Botner, et al; Heterologous Challenge With . . . Infection; Veterinary Microbiology; 68 (1999); p. 187-195.
Hanne Gahery-Segard, et al; Multiepitopic B- and T-Cell . . . Vaccine; Journal of Virology; Feb. 2000; p. 1694-1703.

* cited by examiner

*Primary Examiner*—Stacy B. Chen
(74) *Attorney, Agent, or Firm*—Ladas & Parry LLC

(57) ABSTRACT

The present invention mainly provides a fusion antigen specific for a target cell comprising a ligand moiety which is capable of reacting, recognizing or binding to the receptors on the target cell, a *Pseudomonas* exotoxin A translocation domain II, an antigenic moiety, and a carboxyl terminal moiety which permits combination of the fusion antigen to the endoplasmic reticulum (ER) membrane of the target cell. A method of immunizing an animal using the fusion antigen is also provided.

22 Claims, 15 Drawing Sheets

FUSION ANTIGEN USED AS VACCINE

BACKGROUND OF THE INVENTION

1. Field of the Invention

The invention mainly relates to a fusion antigen. More particularly, the invention mainly relates to a fusion antigen used as a T-cell vaccine.

2. Description of the Related Art

The mechanism of immunization in an animal comprises humoral immunity and cell-mediated immune response.

Humoral immunity mainly relates to the production of antibodies. Antibodies can provide protection from pathogens or their toxic products by binding to them and thereby blocking their access to cells that may be infected or destroyed. Antibodies can also trigger a phagocytic cell to ingest and destroy the pathogen, such as a bacterium. The third function of antibodies is to activate a system of plasma proteins, known as a complement, that can directly destroy bacteria.

Cell-mediated immune reactions depend on direct interactions between T-lymphocytes and cells bearing the antigen that T-cells recognize. These cells recognize body cells infected with viruses, which replicate inside cells using the synthetic machinery of the cell itself. Antigens derived in the replication of a virus, however, are present on the surface of infected cells (by MHC class I), where they are recognized by cytotoxic T-cells ($CD8^+$ T-cells) and these may then control the infection by killing the cells before the replication of a virus is complete.

Vaccines for prophylaxis of viral infections are usually live attenuated organisms with reduced pathogenicity that would stimulate protective immunity. Foreign proteins of a live virus that is used as a live attenuated vaccine, are recognized and processed in the endoplasmic reticulum (ER) lumen of antigen presenting cells (APCs) when the virus replicates to form an endogenous processing peptide. The process includes antigen modification and proper digestion. However, a live attenuated vaccine has a quite strong tendency to recover toxicity. For example, the toxicity of infectious laryngotracheitis virus (ILTV) recovers both in vaccine or attenuated strains. Besides, multiple passages of a virus should be operated; therefore, the ability to evoke an immune response is discredited. It is a time-consuming job to develop a live attenuated vaccine.

To prevent the recovery of a live attenuated vaccine, gene deficient vaccines are developed, such as Aujeszky's disease vaccines, gI negative vaccines, and PRV marker vaccines.

In another aspect, recombinant subunit vaccines and DNA vaccines are also disclosed. Viruses or bacteria of vaccina or fowlpox are used as vectors for carrying the genes of the antigens. Through recombinant DNA technology, the time for development of a good vaccine is reduced and multiple serotypes of vaccine can be achieved at the same time. Examples of such vaccines are fowlpoxvirus and *Salmonella* vector systems and Syntro Vet (US) gene recombinant vaccines. On the other hand, when a microorganism, especially an RNA virus, is used as a vector, the microorganism would derive a new species or a new strain. The safety of such vaccines is challenged. Besides, recombinant subunit vaccines are usually helpless in triggering a cell-mediated immune response. They are exogenous antigens, which are taken into macrophages, dendritic cells and B lymphocytes. Peptides from exogenous antigens are generated after the internalization of the antigens within APCs via fluid phase pinocytosis or membrane-bound receptors. The peptides are generated in the endosomal compartments of the APCs and sorted by empty MHC class II molecules to form peptide-MHC class II complexes based on the affinities between the MHC class II molecules and the peptides. The peptide-MHC class II complexes are then translocated to the surface of the APCs where they are recognized by $CD4^+$ T-cells. However, small subunit proteins recognized by $CD8^+$ T-cells cannot be used efficiently as vaccines because, once parenterally administered, they are internalized in endosomal compartments where they are likely to be either extensively degraded or fail to interact with the MHC class I pathway. Furthermore, $CD4^+$ cells (Th cells) can both activate humoral immunity and cell-mediated immune response by Th1 and Th2 helper T-cells, respectively. Th1 and Th2 cells regulate each other for the balance of humoral immunity and cell-mediated immune response. Therefore, if only humoral antibodies will produce in all the immune responses, viral infection will be less controlled because of over sensitization of an immune system. Fortunately, it is now possible to envisage the preparation of safe T-cell vaccines able to induce protective cell-mediated immunity against all viruses (Constantin A. Bona, et al. 1998. Immunology today vol 19. 126-131).

Vaccines for virus-infecting immunological cells such as T-cell, B-cell, dendritic cell, monocyte, and macrophage still remain to be developed. Examples of such viruses are porcine reproductive and respiratory syndrome virus, Circovirus type II, and human immunodeficiency virus. Such viruses shut down the ability of recognition of foreign proteins as antigens in the antigen presenting cells. The immunological cells cannot function and carry the viruses. This kind of infection usually leads to acute damage to the animal infected. The animals that have been infected are easily infected by other pathogens. A recent report shows that cytotoxic T-cells (CTLs) are essential for controlling HIV infection. (Hanne G-S et al 2000. Journal of virology vol 74, No. 4. p. 1694-1703). It is a pity that a useful vaccine for virus-infecting immunological cells is still lacking.

In particular, porcine reproductive and respiratory syndrome virus (PRRSV) results in high losses in animal husbandry every year. The virus infects macrophages (in the alveolar and spleen), brain microglia and monocytes, and exists in the blood and organs of the infected animals. Antibodies have little effect on the virus and even stimulates mutations of the virus. In the mechanism of antibody dependent enhancement (ADE), the use of antibodies lead to more severe infections. About 50 to 80% of pigs are infected by such virus. Generally, the animals infected by the virus have no significant symptoms, but the immunity of the infected animals will be reduced. This leads to a decrease of weight gain and an increase in death rate. PRRSV is an RNA virus. Not only animals, but also ducks would be infected by PRRSV. A live attenuated vaccine against PRRSV was developed. However, mutation of the viruses in the live vaccine quite often occurs. To develop a safe vaccine is desired.

SUMMARY OF THE INVENTION

The present invention provides a fusion antigen which can be used as a T-cell vaccine, and preferably, as a T-cell vaccine against the virus-infecting immunological cells. The invention is characterized by the design of carboxyl terminal moiety of the fusion antigen.

One objective of the invention is to provide a fusion antigen specific for a target cell comprising an antigenic moiety, a ligand moiety which is capable of reacting, recognizing or binding to the receptors on the target cell, a

*Pseudomonas* exotoxin A translocation domain II, and a carboxyl terminal moiety which permits retention of the fusion antigen in the endoplasmic reticulum (ER) membrane of the target cell.

Another objective of the invention is to provide a pharmaceutical composition comprising the fusion antigen of the invention together with a pharmaceutically acceptable carrier.

Still another objective of the invention is to provide a method of immunizing an animal comprising the steps of:
(a) providing a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the endoplasmic reticulum (ER) membrane of the target cell; and
(b) inoculating the animal with the fusion antigen.

DETAILED DESCRIPTION OF THE INVENTION

Figure 1:
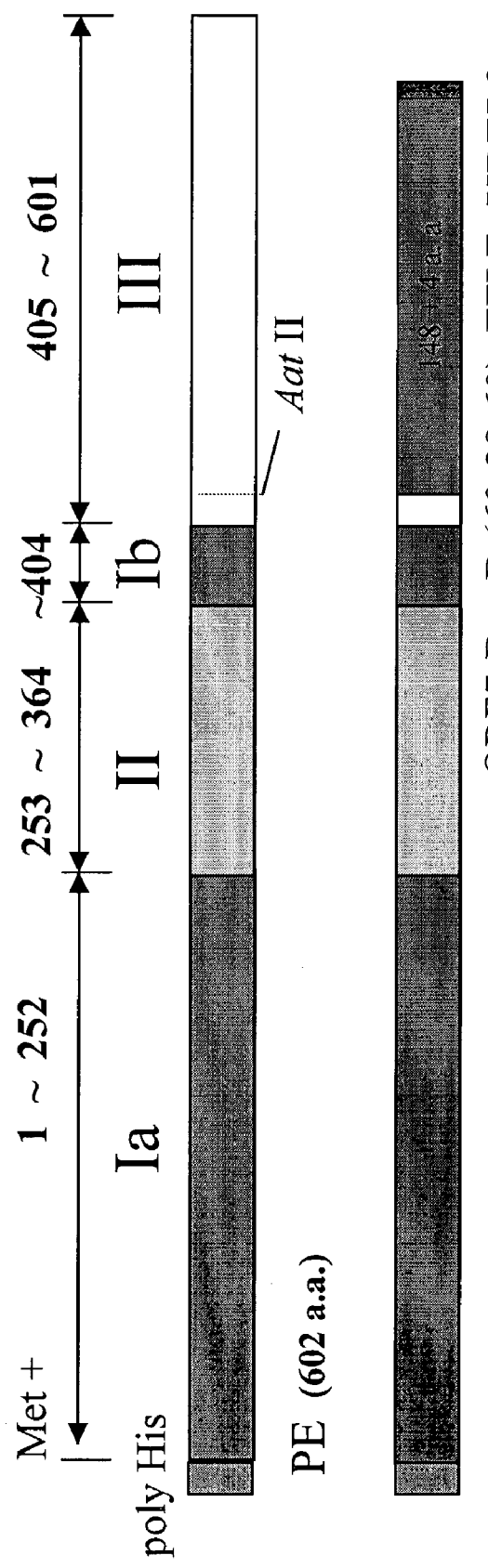
FIG. 1 illustrates the construction of PRRSV ORF 7 fusion antigen according to Example 1.

The invention provides a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the endoplasmic reticulum (ER) membrane of the target cell.

As used herein, the term "fusion antigen" refers to a recombinant protein which can evoke an immune response in an animal. Preferably, the fusion antigen comprises epitopes for evoking an immune response directly and other portions for enhancing an immune response such as mediating delivery, transporting, processing, and expressing or for equipment of multiple functions.

Preferably, the target cell is an antigen presenting cell. More preferably, the target cell is selected from the group consisting of T-cells, B-cells, dendritic cells, monocytes, and macrophages.

As used herein, the term "an antigenic moiety" refers to a peptide fragment that can evoke an immune response. In one embodiment of the invention, the antigenic moiety is an epitope. According to the invention, the antigenic moiety is a protein of a pathogenic species, which can highly activate an immune response. Such proteins comprise, for example, but are not limited to, coat proteins, nucleoproteins or cell membrane proteins. The antigenic moiety can be a peptide cloned directly from the pathogenic species as well as a recombinant protein modified by artisans skilled in the field for enhancing the ability to evoke an immune response, for being manufactured more conveniently and for being delivered more easily. Preferably, the antigenic moiety is derived from porcine reproductive and respiratory syndrome virus (PRRSV), Circovirus type II, or human immunodeficiency virus. Preferably, the antigenic moiety may be PRRSV ORF 1, 2, 3, 4, 5, 6, or 7. In one more preferred embodiment of the invention, the antigenic moiety is PRRSV ORF 7. For evoking a more severe immune response, the antigenic moiety comprises at least one antigenic unit and the adjacent antigenic unit is connected by a bridge region. According to the invention, the bridge region may be a small fragment of peptide that evokes little immune response to prevent the immune system from recognizing it.

As used herein, the term "ligand moiety" refers generally to all molecules which are capable of reacting, recognizing or binding to the receptor on a target cell. Examples of such receptors include, but are not limited to, antibody receptors, growth factor receptors, lymphokine receptors, cytokine receptors, hormone receptors and the like. In some embodiments of the invention, the receptor for binding to the ligand moiety is selected from the group consisting of TGFα receptors, IL2 receptors, IL4 receptors, IL6 receptors, IGF 1 receptors, CD4 receptors, IL18 receptors, IL 12 receptors, EGF receptors, LDL receptors and α2-macroglobulin receptors. The ligand moiety has an ability of binding to the cell membrane of the target cell for anchoring the fusion antigen to the target cell. The immune system is initiated by the fusion antigen's binding to the receptors on the target cell. Preferably, the ligand moiety is a *Pseudomonas* exotoxin A binding domain I. *Pseudomonas* exotoxin A (PE) is a single polypeptide chain of 613 amino acids. X-ray crystallographic studies and mutational analysis of the PE molecule show that PE consists of three domains: an amino terminal cell receptor binding domain (Domain I); a middle translocation domain (Domain II); and a carboxyl terminal activity domain (Domain III) (see U.S. Pat. No. 5,705,163, which is incorporated into references).

As used herein, the term "*Pseudomonas* exotoxin A binding domain I" refers to a peptide fragment that has the same sequence as the amino terminal cell receptor binding domain of *Pseudomonas* exotoxin A or a functionally equivalent fragment. The amino terminal cell receptor binding domain of *Pseudomonas* exotoxin A comprises two sub-domains, designated as domain Ia and domain Ib. The configuration of domain Ia and domain Ib can bind to a LDL receptor or α-macroglobulin receptor on a cell surface. As used herein, the term "*Pseudomonas* exotoxin A binding domain II" refers to a peptide fragment that has the same sequence as the middle translocation domain of *Pseudomonas* exotoxin A or a functionally equivalent fragment. The *Pseudomonas* exotoxin A translocation domain II has an ability to translocate the fusion antigen into the cytoplasm of the target cell. The fusion antigen is translocated into the target cell after attaching to the target cell membrane.

As used herein, the term "carboxyl terminal moiety which permits retention of the fusion antigen to the endoplasmic reticulum (ER) membrane of a target cell" refers to a peptide fragment that enables the fusion antigen to bind to the ER membrane and to retain it in the ER lumen. In one embodiment of the invention, the carboxyl terminal moiety comprises, in a direction from the amino terminus to the carboxyl terminus, the following amino acid residues:

$R^1\text{-}R^2\text{-}R^3\text{-}R^4\text{-}(R^5)_n$

Wherein,
$R^1$ is a positively charged amino acid residue;
$R^2$ is a negatively charged amino acid residue;
$R^3$ is a negatively charged amino acid residue;
$R^4$ is L;
$R^5$ is a positively charged amino acid residue; and
n is 0 or 1.

Preferably, the carboxyl terminal moiety is a member of the KDEL family protein. As used herein, the term "KDEL family protein" refers to a group of proteins, which has a similar carboxyl end binding to the ER membrane of a cell and further has an ability for retention of such protein in the ER lumen. Generally, the length of the carboxyl end ranges from 4 to 16 residues. As discussed in U.S. Pat. No. 5,705,163 (which is incorporated into the references), the amino residues at the carboxyl end of a KDEL family protein, particularly those in the last five amino acids, are important. As shown in the studies on the similar sequences present in different molecules and performing a specific biological function, a sequence that retains a newly formed protein within the endoplasmic reticulum is LysAspGluLeu. These findings suggest that the sequence at the carboxyl end of the fusion antigen according to the invention acts as some type of recognition sequence to assist translocation of the fusion antigen from an endocytic compartment into the ER and retains it in the lumen. In a preferred embodiment, the carboxyl terminal moiety comprises a sequence of KDEL (SEQ ID NO: 11). In a more preferred embodiment, the carboxyl terminal moiety comprises a sequence of KKDL-RDEL-KDEL (SEQ ID NO: 10).

The invention is characterized by the design of carboxyl terminal moiety, which enables the fusion antigen to be processed in the ER of the target cell for combining with MHC class I molecules and being recognized by T-cells. The fusion antigen according to the invention is useful in triggering cell-mediated immune reactions.

According to the invention, the fusion antigen is used for the immunization of animals. One objective of the invention is to provide a pharmaceutical composition comprising the fusion antigen of the invention together with a pharmaceutical acceptable carrier. Preferably, the pharmaceutical composition is a T-cell vaccine.

As used herein, the term "T-cell vaccine" refers to a vaccine that can protect a subject from infection by activating cell-mediated immune response. The crucial role of the T-cell vaccine is cytotoxic T-cell (also known as cytotoxic T lymphocyte, CD8+ T-cell, and CTL) and memory T-cells ($T_{cm}$ and $T_{em}$).

The present invention also provides a method of immunizing an animal comprising the steps of:
(a) providing a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the endoplasmic reticulum (ER) membrane of the target cell; and
(b) inoculating the animal with the fusion antigen.

In the Step (b) of the method, the animals may be inoculated with the fusion antigen in any way known to artisans skilled in this field. For example, the fusion antigen may be delivered by injection or in a form of oral vaccine. Booster shots are optional, if necessary. Preferably, the inoculation is performed before infection. Newly born animals, even an embryo, may also be inoculated with the fusion antigen to produce better immunity.

According to the invention, the following actions occur during the process of the response to the immunization:
(c) the target cell membrane binds to the ligand moiety for anchoring the fusion antigen to the target cell;
(d) the fusion antigen is translocated into the cytoplasm of the target cell by the *Pseudomonas* exotoxin A translocation domain II;
(e) the ER membrane of the target cell binds to the carboxyl terminal moiety of the fusion antigen for retention of the fusion antigen in the ER lumen;

(f) the antigenic moiety is processed in the ER lumen;
(g) the processed antigenic moiety binds with a MHC class I molecule;
(h) the processed antigenic moiety is carried by the MHC Class I molecule to the target cell surface;
(i) the processed antigenic moiety carried by the MHC class I molecule by CD8$^+$ T-cell is recognized to obtain an immune message; and
(j) the immune message is stored by memory T-cells for immunizing the animal.

In Action (c), the ligand moiety of the fusion antigen leads the fusion antigen to bind to the receptors on the target cell membrane for anchoring the fusion antigen to the target cell.

In Action (d), the fusion antigen is translocated into the cytoplasm of the target cell by the *Pseudomonas* exotoxin A translocation domain II. The translocation leads the fusion antigen to entry into the target cell.

In Action (e), the carboxyl terminal moiety of the fusion antigen binds to the ER membrane of the target cell for retention of the fusion antigen in the ER lumen for the process of the fusion antigen.

In Action (f), the antigenic moiety is processed in the ER lumen. The process includes, but is not limited to, antigen modification such as glycosilation and proper digestion by enzyme in the ER lumen.

In Action (g), the processed fusion antigen can bind to a MHC class I molecule. The MHC class I molecule itself is an uncompleted folding protein and binds to many chaperones. The processed fusion antigen binds to the peptide-binding cleft to complete folding and stimulates the release of the chaperones.

In Action (h), the processed antigenic moiety is presented to the target cell surface by the MHC class I molecule. The folded MHC class I and processed antigenic moiety is delivered to the cell surface.

In Action (i), the processed antigenic moiety carried by the MHC class I molecule was recognized by CD8$^+$ T-cell to obtain an immune message for the recognition of the cytotoxic T-cell and also for the storage an immune message into memory T-cells. Examples of the memory T-cells are T$_{cm}$ and T$_{em}$ cells.

In Action (j), the immune message is stored by memory T-cells for immunizing the animal. When the animal immunized with the fusion antigen is infected by the same antigen again, the memory T-cells evoke a stronger immune response in a shorter time. T-cell vaccine provides an endogenous processing antigen which can be processed in the ER lumen of the target cell.

The present also provides a fusion porcine reproductive and respiratory syndrome virus (PRRSV) ORF 7 antigen comprising a PRRSV ORF 7 moiety; a *Pseudomonas* exotoxin A binding domain I; a *Pseudomonas* exotoxin A translocation domain II; and a carboxyl terminal moiety which permits retention of the fusion antigen in the endoplasmic reticulum (ER) membrane of a target cell.

A pharmaceutical composition comprising the fusion antigen of the invention together with a pharmaceutically acceptable carrier is also provided.

Another aspect of the invention is to provide a method of immunizing an animal for the prevention of porcine reproductive and respiratory syndrome virus (PRRSV), which comprises the steps of:
(a) providing a fusion antigen comprising a PRRSV ORF 7 antigen moiety, a *Pseudomonas* exotoxin A binding domain I, a *Pseudomonas* exotoxin A translocation domain II, and a carboxyl terminal moiety which permits retention of the antigen in the endoplasmic reticulum (ER) membrane of an target cell; and
(b) inoculating the fusion antigen into the animal.

The following examples are given for the purpose of illustration only and are not intended to limit the scope of the present invention.

EXAMPLE 1

PRRSV ORF 7 Fusion Antigen

Figure 2:
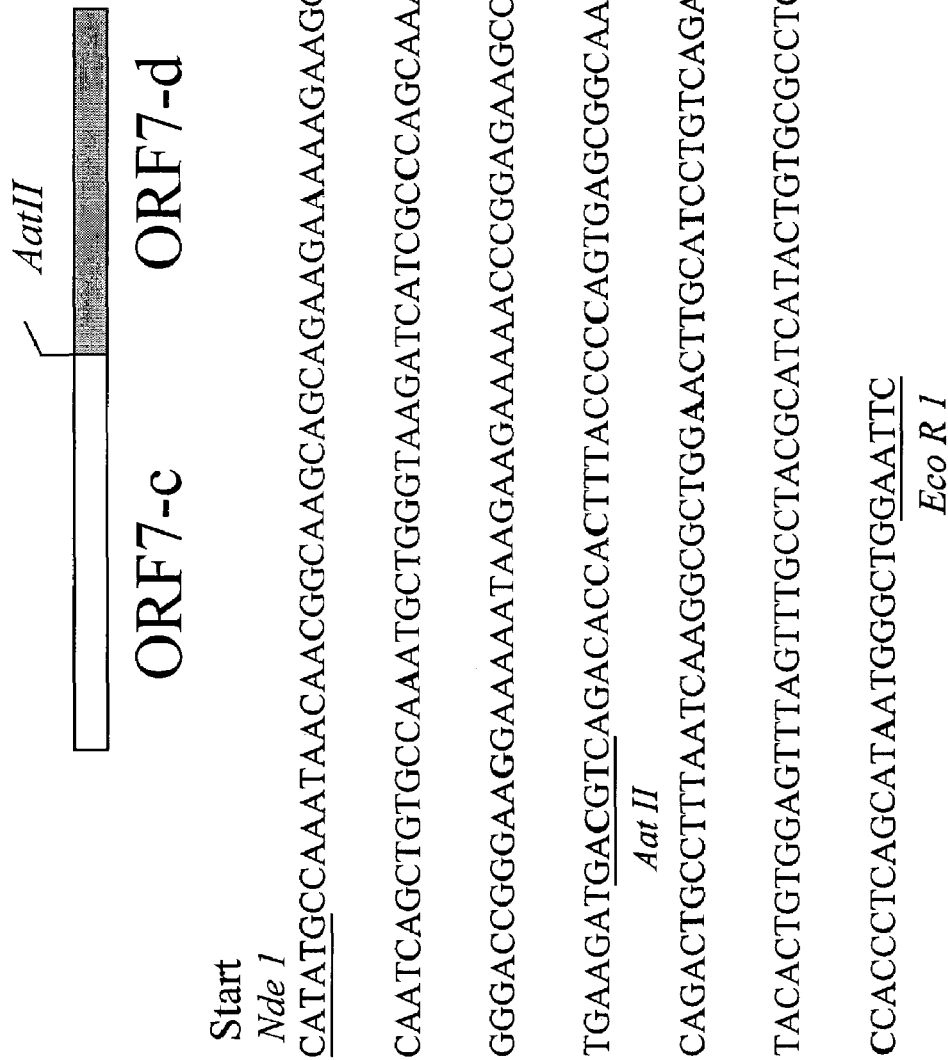
FIG. 2 illustrates the gene sequence of PRRSV ORF 7 (SEQ ID NO: 1).

Antigenic moiety: The nucleoprotein PRRSV ORF 7 gene sequence was as shown in SEQ ID NO: 1 (Genbank Acc. No. AF035409, also shown in FIG. 2). The PRRSV ORF 7 gene was cloned with specific primers, which were the forward primer, 5'-GTC ACA TAT GCC AAA TAA CAA CGG CA-3' (SEQ ID NO: 2) and the reversed primer, 5'-AAG AAT TCC AGC TCA TCC ATG CTG-3' (SEQ ID NO: 3). An Aat II restriction enzyme recognition site was used for ligation and insertion to a *Pseudomonas* exotoxin A translocation domain II.

*Pseudomonas* exotoxin A binding domain I and *Pseudomonas* exotoxin A translocation domain II: pJH4 was used as a starting plasmid, which encodes the *Pseudomonas* exotoxin A (PE) full-length gene as described by Liao C. W. et al. (Liao C. W. et al., 1995. Applied Microbiol Biotechnol 43: 498-507). The Nde I-Eco R I DNA fragment of the full length of PE gene including domain I, II and III was constructed into pET 15 derivative plasmid to form a pET-PE plasmid, which has one Eco R I and Xho I restriction enzymes recognition sites at the 3'-end of PE gene.

Figure 3:
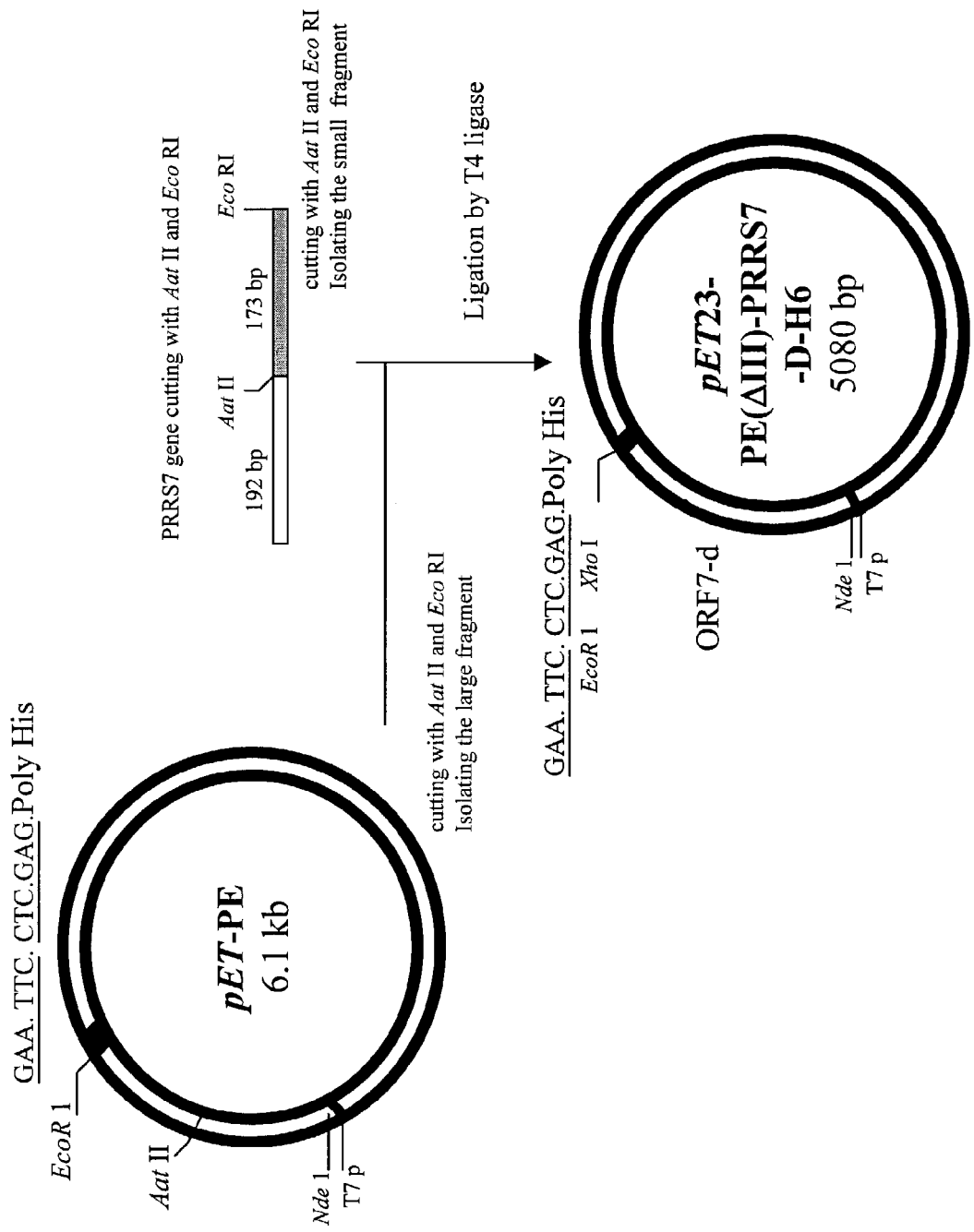
FIG. 3 illustrates the construction of PE-PRRS7-D in pET23a protein expression plasmid.

Fusion PE(III) with antigen gene: The 192 bp of Aat II-Eco R I fragment (named D fragment), which is a C terminal DNA fragment of PRRSV ORF 7 nucleoprotein gene, was obtained by RT-PCR and digested with Aat II and Eco R I restriction enzymes. The DNA fragments were then purified by gel electrophoresis and electro-elution. This D fragment and the 7.1 kb Aat II-Eco R I large fragment of pET-PE plasmid were ligated with T4 ligase to form a plasmid pET15-H6-PE(ΔIII)-PRRS7-D (7.31 kb). The plasmid comprised Eco R I and Xho I recognition sites at the end of the fusion gene. For increasing antigenicity, a DNA fragment with two tandem repeated D fragments connected with a bridge (g) was created (named DGD) according to recombinant technique. A 7,7-kb plasmid encoding PE(ΔIII)-PRRS7-DgD (as shown in FIG. 3) was then constructed by the ligation of the Sal I-DgD-Pst I fragment with a 6.0-kb Sal I-Pst I fragment of pET 15-H6-PE(ΔIII)-PRRS7-D (named PE-DGD).

Figure 4:
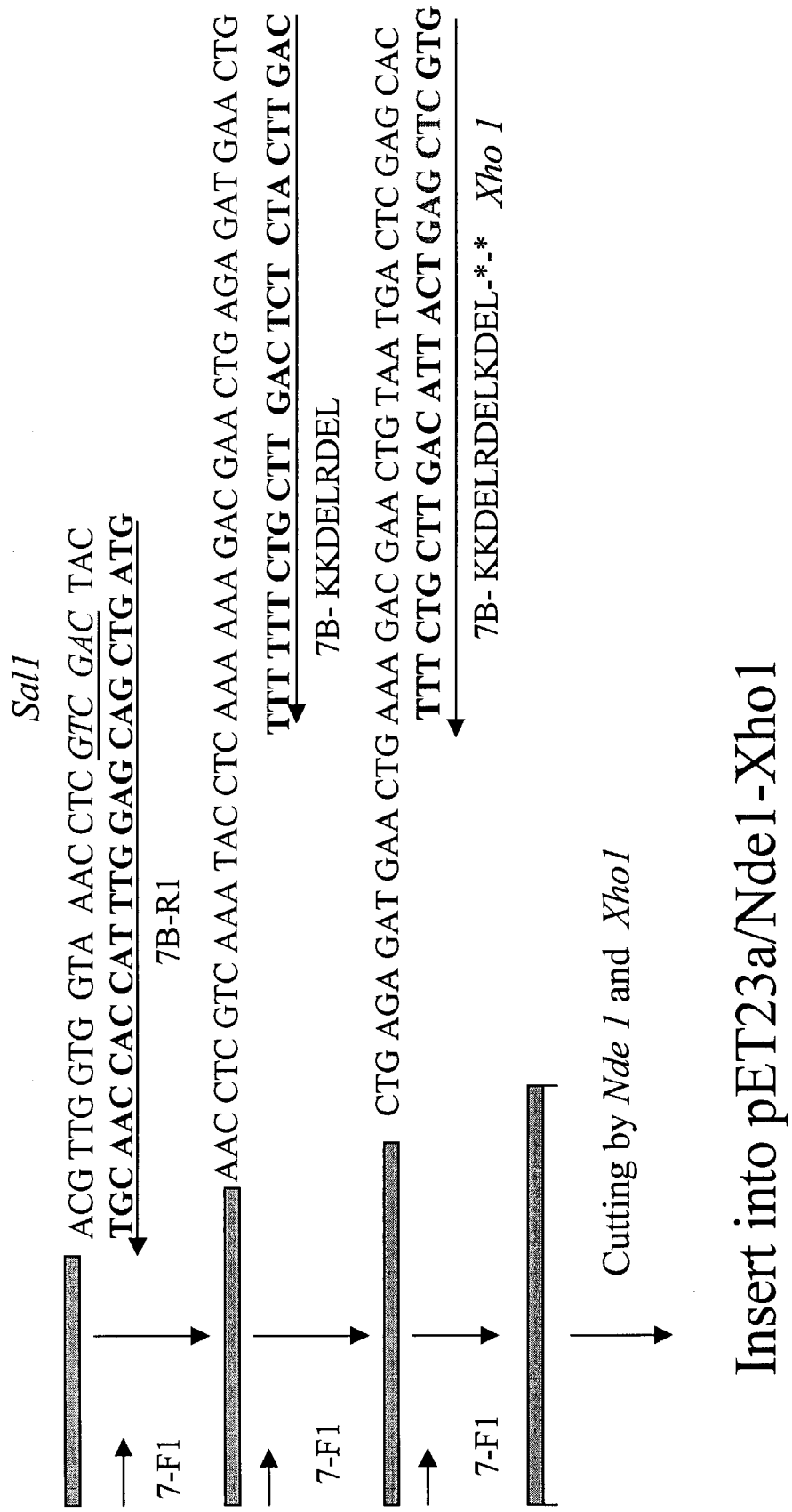
FIG. 4 illustrates the construction of pET23-3 KDEL. The sequence KKDELRDEL is amino acids 1-9 of SEQ ID NO: 4. The sequence KKDELRDELKDEL is SEQ ID NO: 4.
Figure 5:
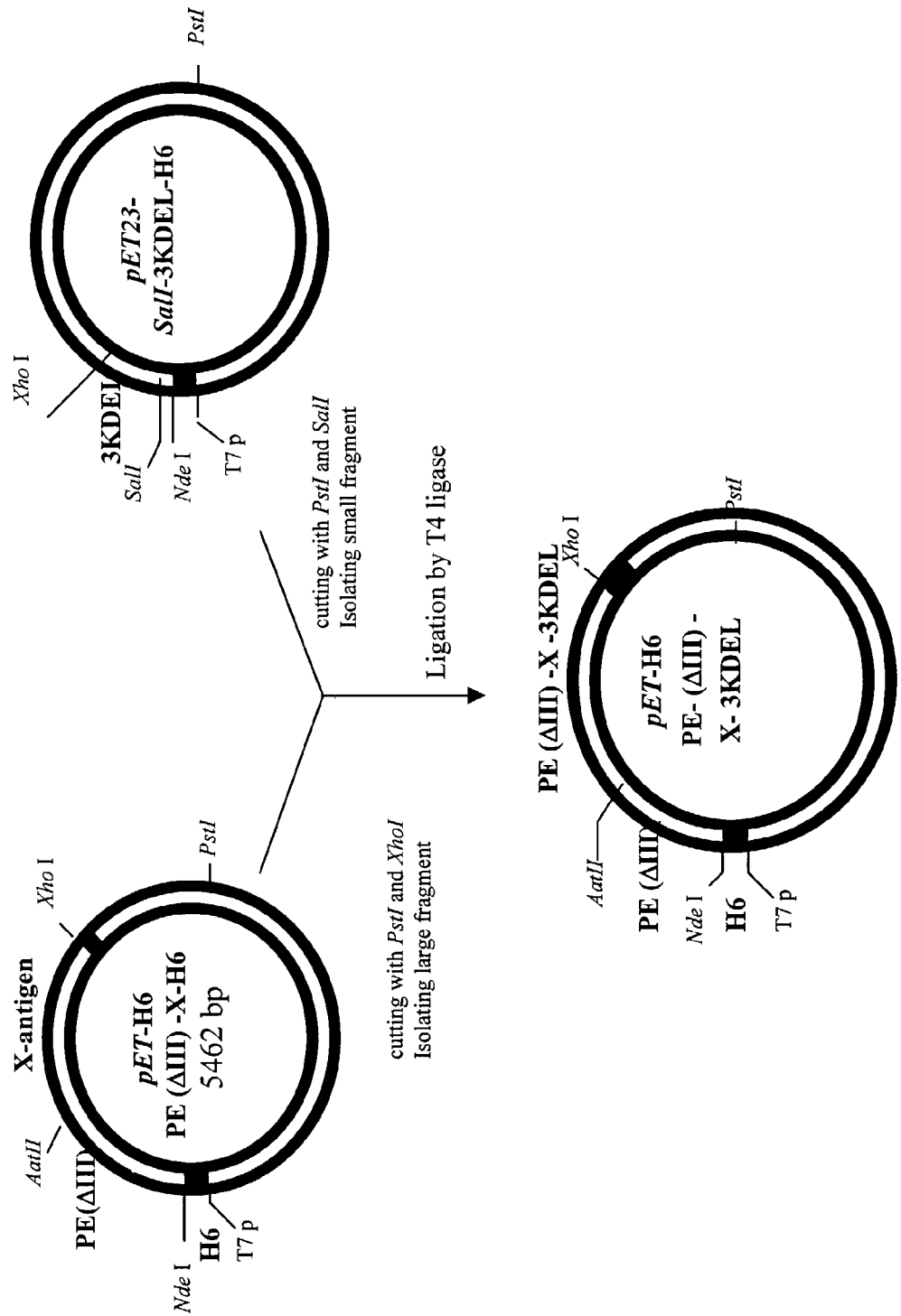
FIG. 5 illustrates the construction of PRRSV ORF 7 fusion antigen.

Carboxyl terminal moiety: Gene sequence coding KKDELRDELKDEL (SEQ ID NO: 4) was shown in SEQ ID NO: 5. A Sal I restriction enzyme recognition site at 5' end and a stop codon TAA-TGA at 3' end were also created (as shown in FIG. 4) and inserted into pET 23a plasmid digested with Nde I and Xho I to form pET23-3 KDEL plasmid (as shown in FIG. 5). Synthesizing a polynucleotide encoding Sal I site-KKDELRDELKDEL-stop codon-Xho I-Eco R I sequence through serial polymerase chain reaction (PCR). The linear DNA of pET23 cutting with Sal I as PCR DNA template, a 168 bp fragment of first PCR product was generated by T7 promoter primer and a reversed primer 5'-TTC ATC TCT CAG TTC GTC TTT TTT GAG GTA GTCGAC GGA GCT CGA ATT CGG-3' (SEQ ID NO: 6). This DNA product contained a Sal I recognition site. Then, the 168 bp of DNA as a second PCR template, one 206 bp fragment of a second PCR product was generated by the T7 promotor primer and a reversed primer 5'-A GAATTC CTCGAG TCA TTA CAG TTC GTC TTT CAG TTC ATC TCT CAG TTC GTC-3' (SEQ ID NO: 7). The final PCR DNA fragment containing Sal I, Xho I, and Eco R I sites was obtained. The PCR-amplified DNA fragments were cleaved with Sal I and Eco R I and then purified by gel electrophoresis and electro-elution. The purified Sal I-Eco R I DNA fragments were ligated to the 3.6 kb of Sal I-Eco R I DNA fragment obtained from pET23a. Finally, the plasmid pET23-Sal I-3 KDEL, encoding Sal1-KKDELRDELKDEL-stop codon-Xho I-Eco R I, was constructed.

Fusion antigen: The PRRSV ORF 7 fusion antigen was shown in FIG. 1.

Two DNA fragments were prepared. One 6.4-kb Pst I-Xho I fragment from plasmid pET15-H6-PE(ΔIII)-PRRS7-DgD (7.7 kb) containing PE(ΔIII) and antigen was obtained by digesting with Pst I and Xho I. Another 1.345-kb Pst I-Xho I fragment containing the carboxyl terminal moiety was also obtained by digesting plasmid ET23-3 KDEL with Pst I and Sal I restriction enzymes. These two fragments were purified and then ligated by T4 ligase to form pET23-H6-PE(Δ III)-DgD-3 KDEL (named PE-DGDk; as shown in FIG. 5).

Protein expression and purification: E. coli BL21 (DE3) pLys cells harboring plasmid for the expression of PE-DGD and PE-DGDk molecules were cultured in Luria Bertani broth containing 100 to 500 ppm of ampicillin at 37° C. When the culture attending early log phase, (A600=0.1 to 0.4), isopropyl-1-thio-β-D-galactopyranoside (IPTG) was added with a final concentration of 0.5 mM for induction. Cells were harvested after induction after 2 hours and immediately stored at −70° C. The fusion antigen was partially purified by urea extraction as described previously (Liao et al., 1995. Appl. Microbiol. Biotechnol. 43: 498-507). Under denaturing conditions, the PE-DGD and PE-DGDk molecules containing 6 x His tag were fully exposed for improving binding to the Ni-NTA matrix (Ni-NTA agarose; Qiagen® Lnc. CA). Therefore, the efficiency of the purification was maximized by reducing the potential for nonspecific binding. Batch purification of 6×His-tagged PE-DGD and PE-DGDk from E. coli under denaturing conditions was as described below:

adding 1 mL of the 50% Ni-TNA slurry to 4 mL lysate and mixing gently by shaking (e.g., 200 rpm) for 60 min at room temperature to form a lysate-resin mixture;

loading the lysate-resin mixture carefully into an empty column with the bottom cap still attached;

removing the bottom cap and collecting the flow-through solution;

washing twice with 4 mL wash buffer (100 mM $NaH_2PO_4$, 10 mM Tris-HCl, 8 M urea, pH 8.0);

eluting the protein 4 times with 0.5 ml pH 5.9 elution buffer (100 mM $NaH_2PO_4$, 10 mM Tris-HCl, 8M urea, pH 5.9) followed by 4 times with 0.5 ml pH 4.5 elution buffer buffer (100 mM $NaH_2PO_4$, 10 mM Tris-HCl, 8 M urea, pH 4.5); and collecting fractions and subjecting to SDS-PAGE.

Figure 6:
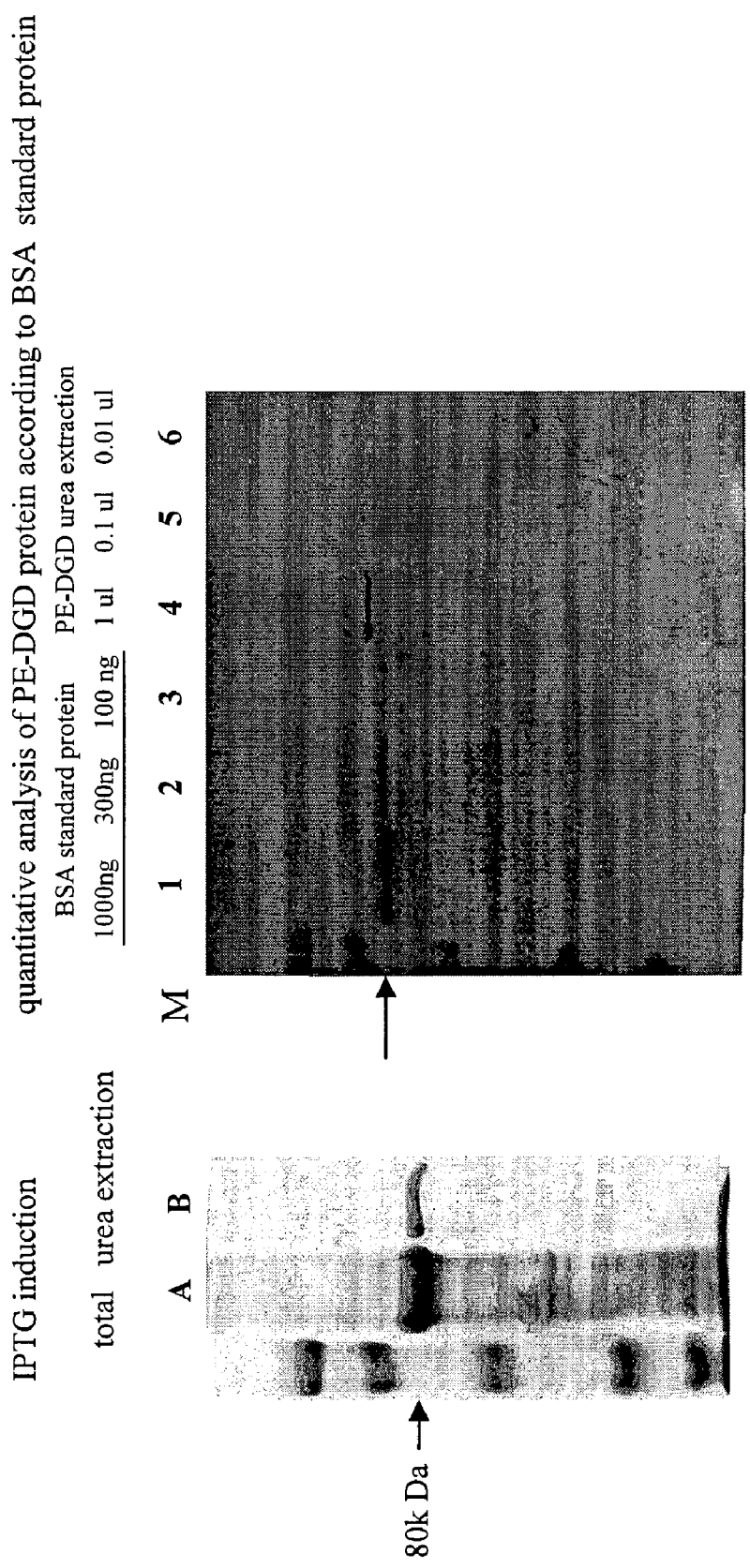
FIG. 6 illustrates the SDS-PAGE detection of protein purification and quantitative analysis for the sample of PE-DGD protein. The PE-DGD protein gene of a PE($\Delta$III) and PRRSV ORF-7 chimeria in pET plasmid system is expressed in BL21(DE3)plys by IPTG induction. The SDS-PAGE maps of the total bacterial proteins are shown after the IPTG induction sample (Lane A) and the urea extraction sample (Lane B or Lane 4). One strong staining band located at 80 K Da is PE-DGD protein. Lanes 1, 2 and 3 are the samples of standard BSA protein loaded with the amounts of 1000 ng, 300 ng and 100 ng, respectively. Lanes 4, 5 and 6 are the samples of PE-DCD urea extraction protein with the amounts of 1 μL, 0.1 μL and 0.01 μL, respectively.
Figure 7:
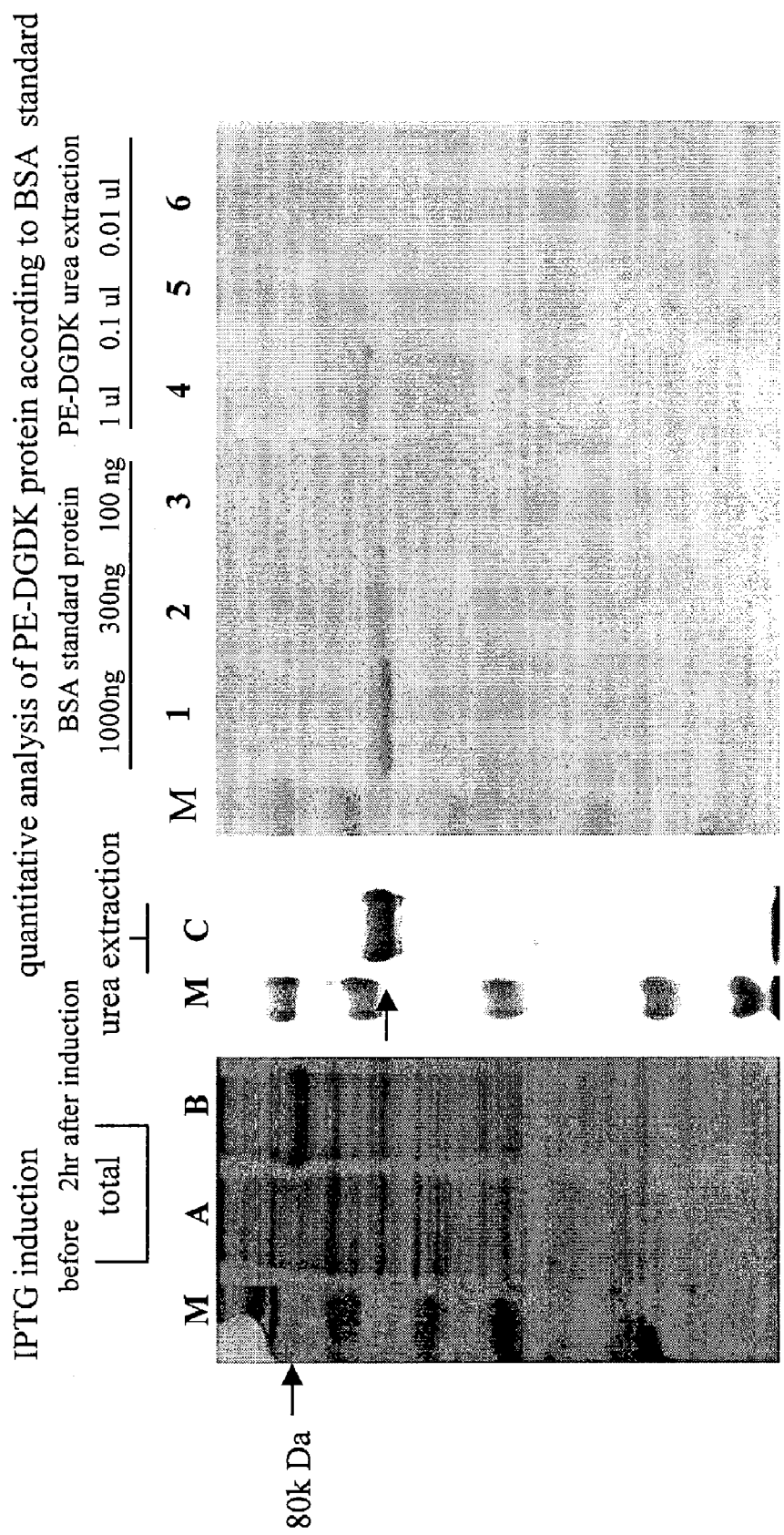
FIG. 7 illustrates the SDS-PAGE detection of protein purification and quantitative analysis for the sample of PE-DGDK protein. The PE-DCDK protein gene of a PE($\Delta$III) and PRRSV ORF-7 chimeria in pET plasmid system is expressed in BL21(DE3)plys by IPTG induction. The SDS-PAGE maps of the total bacterial proteins are shown for the samples before (Lane A) and after IPTG induction (Lane B) and the urea extraction sample (Lane C or Lane 4). One strong staining band located at 80 K Da is PE-DGDK protein. Lanes 1, 2 and 3 are the samples of standard BSA protein loaded with the amounts of 1000 ng, 300 ng and 100 ng, respectively. Lanes 4, 5 and 6 are the samples of PE-DGDK urea extraction protein with the amounts of 1 μL, 0.1 μL and 0.01 μL, respectively.

The results are shown in FIGS. 6 and 7. Quantitative analysis was performed using standard BSA protein. It showed that the fusion antigen was successfully constructed.

EXAMPLE 2

PRRSV ORF 7 Fusion Antigen as T-Cell Vaccine

The preparation of PRRSV ORF 7 fusion antigen used herein are described in Example 1.

Animals: Pigs were obtained from a herd periodically tested for PRRSV and known to be free of the virus by RT-PCR. Blood plasma fractions were collected. The RNA was extracted with a kit of NucleoSpin RNA II™ (Macherey-Nagel GmbH & Co. KG, Germany). RA1 solution of 350 μL and 3.5 μL of □β-mercaptoethanol were added into 100 μL plasma fractions. After reducing viscosity and clearing the lysate by filtration, the lysate was mixed with 350 μL of 70% ethanol. The RNA was adsorbed in Nucleospin™ RNA column by centrifugation and followed by a wash. Ninety-five μL DNase solution was applied into the column for the digestion of DNA. After repeating the wash and centrifugation several times, RNA was eluted by 60 μL Rnase-free water.

RT-PCR was performed by using Qiagen Onestep RT-PCR Kit™ (Qiagen® Inc. CA). A forward primer of 5'-CCA GCC AGT CAA TCA GCT GTG-3' (SEQ ID NO: 8) and a reverse primer of 5'-GCG GAT CAG GCG CAC-3' (SEQ ID NO: 9) were provided for synthesizing a 293-bp fragment. The detection limit of RT-PCR by agarose gel electrophoresis was determined around 10 of PRRS ($TCID_{50}$/ml).

Figure 8:
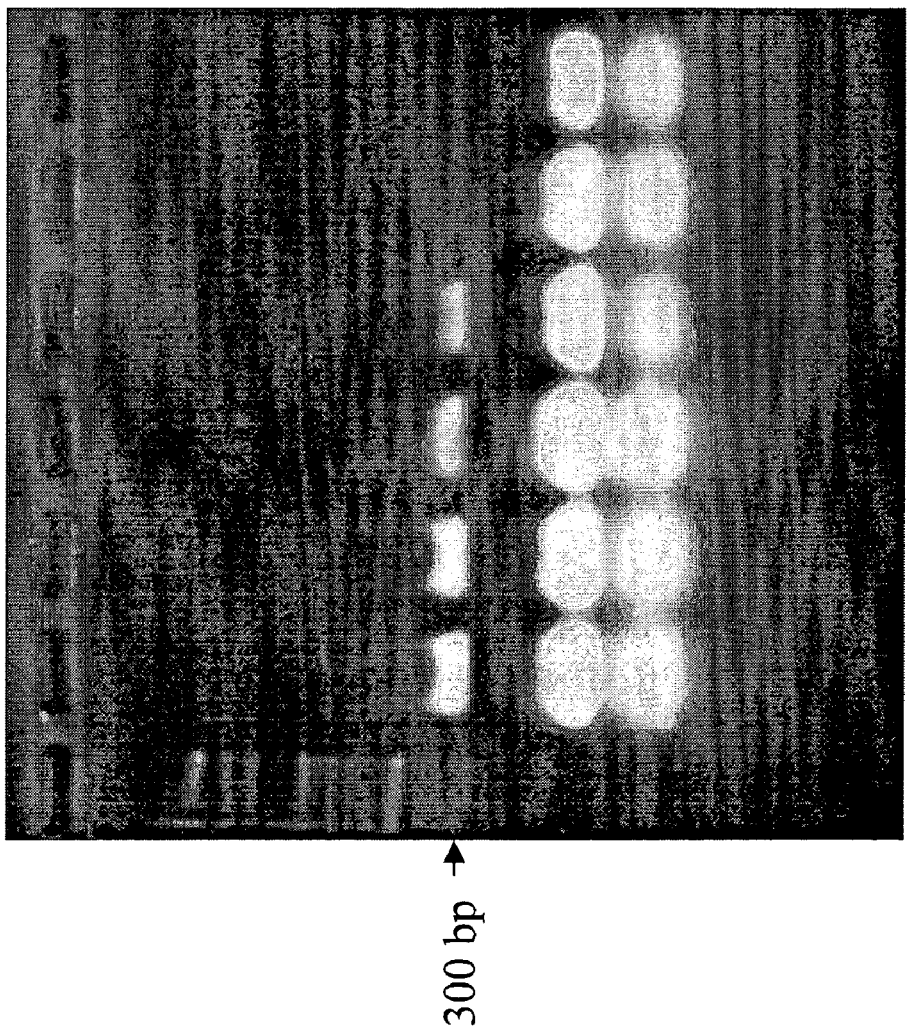
FIG. 8 illustrates the detection limit of RT-PCR with BM-ORF7 primers in pig blood leukocyte sample. The total RNA of 100 μL pig blood leukocyte samples with 1 μL 3-fold serial dilution of PRRS virus (106 TCID$_{50}$/ml) were respectively extracted. The PRRSV detection limit was determined by RT-PCR running with BM-ORF7 primers and 10/25 volume RNA template. The RT-PCR products of the spike samples containing approximately 300, 100, 30, 10, 3, 1 (TCID$_{50}$/ml) of PRRS, were loaded as Lane 1, 2, 3, 4, 5, 6, respectively, and running at 2% agarose gel in TBE buffer.
Figure 9:
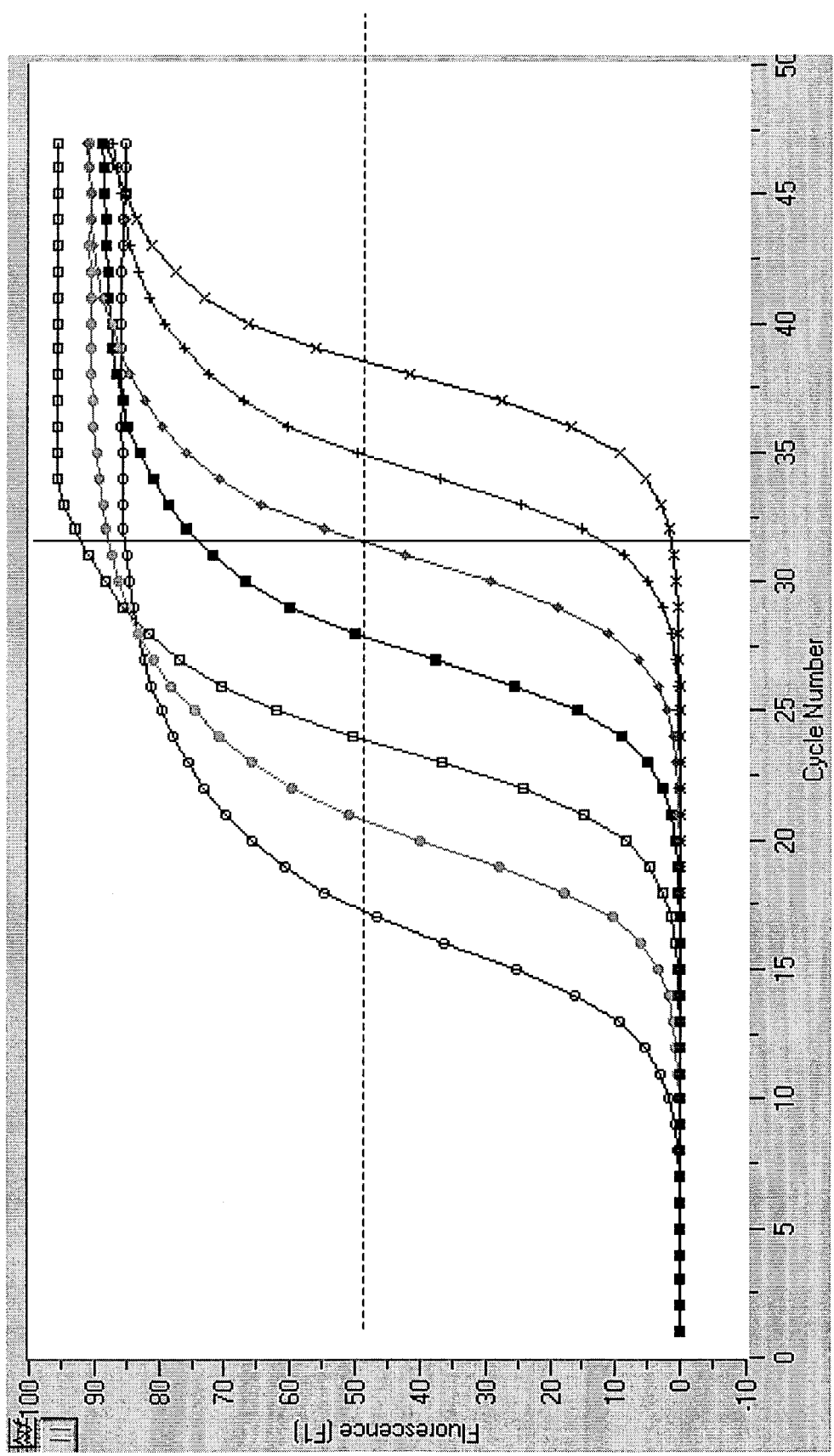
FIG. 9 illustrates the result of the real time PCR analysis of PRRSV by BM-primers.
Figure 10:
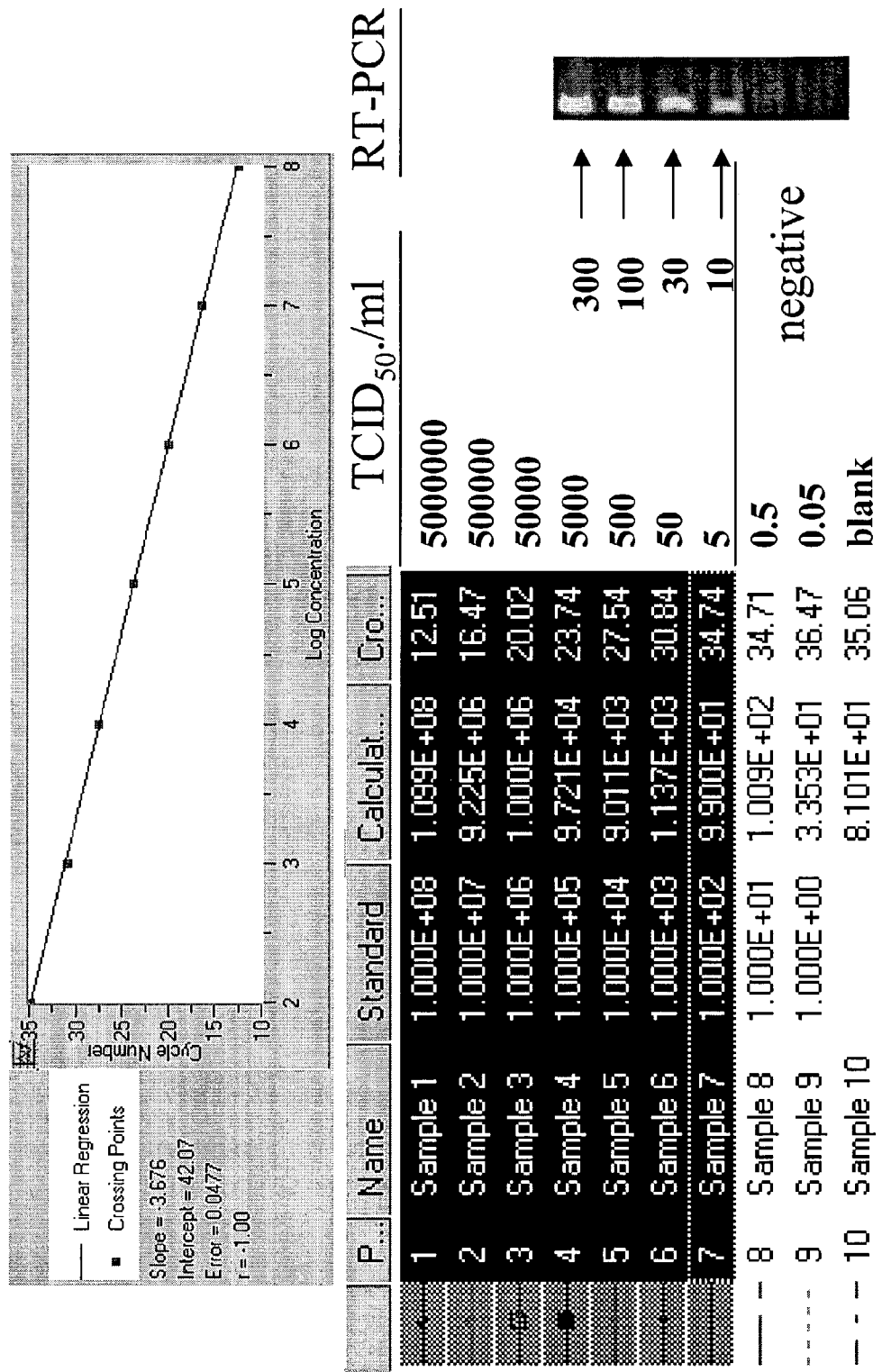
FIG. 10 illustrates the result of the comparison of the detection limit of real-time PCR with tradition RT-PCR.
Figure 11:
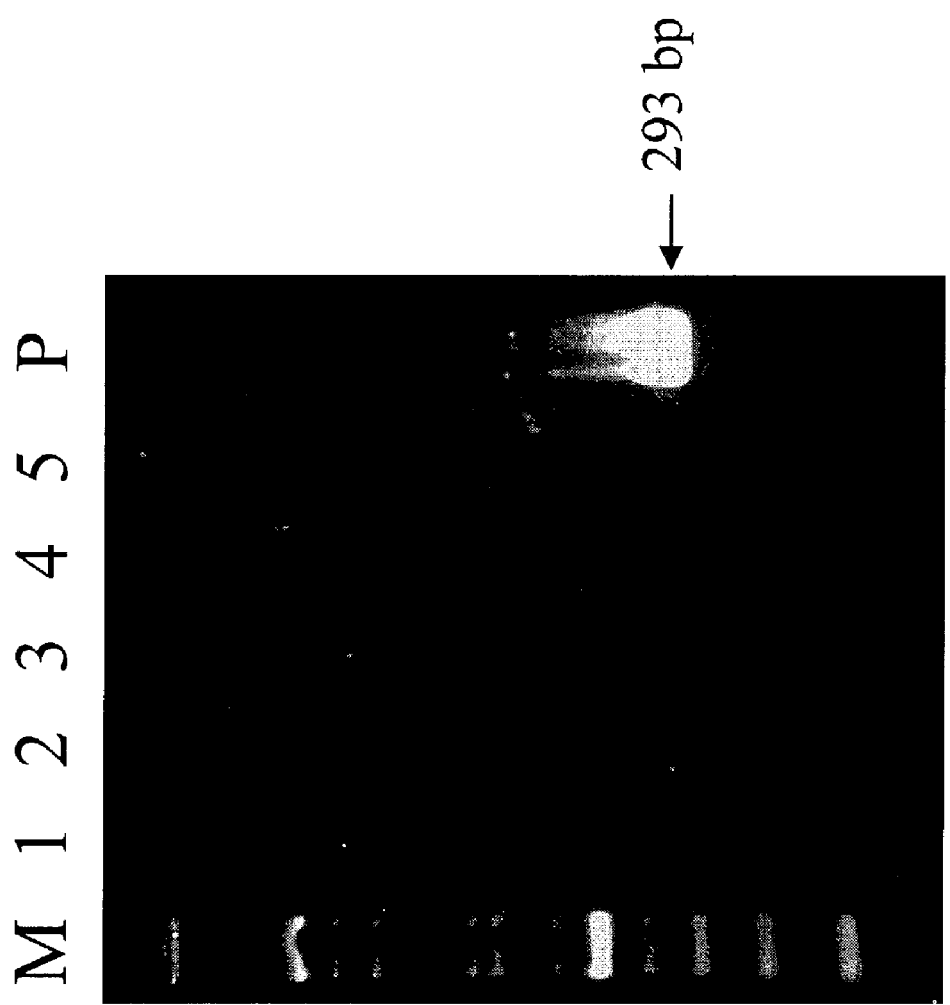
FIG. 11 illustrates the result of the detection of PRRSV by RT-PCR of five female pigs, wherein M represents the DNA marker and P represents the positive control.

Blood leukocyte samples derived from five sows in a SPF farm were subjected to RT-PCR. It showed that the five sows were not infected with PRRSV. The results are shown in FIGS. 8 to 10.

Immunization: Six new-born piglets were selected and individually identified, weighed, and sexed from each of the three sows in a SPF farm. The piglets were randomly sub-grouped into three groups of vaccinated with PE-DGD, vaccinated with PE-DGDK and control based upon weight stratification, wherein each group comprised two piglets from each sow. In the vaccinated groups, intramuscular immunization was performed twice at the suckling stage. At the weaning stage (approximately 3 to 4 weeks of age), each group was removed and housed in an isolation room equipped with air conditioning and ventilation. The vaccinated group was immunized twice at ages 4 and 18 days by intramuscular injection with 2 mL of vaccine containing 1 mL of PE-DGD or PE-DGDK (containing 50 μg protein/dose) emulsified in 1 mL ISA206 (SEPPIC®, France), respectively. The control group was raised without immunization.

Challenge in pig model: Two weeks after the final vaccination, the pigs were intranasally challenged after intramuscular administration of 100 mg of Ketamine solution for sedation followed by intranasal instillation of 1 ml of 2% Lidocaine for cough-reflex suppression. Fresh 1 mL of MD-1 strain of PRRSV culture was used for challenge at doses of about $1×10^7$ $TCID^{50}$/mL. Five piglets were challenged in each group.

Figure 12:
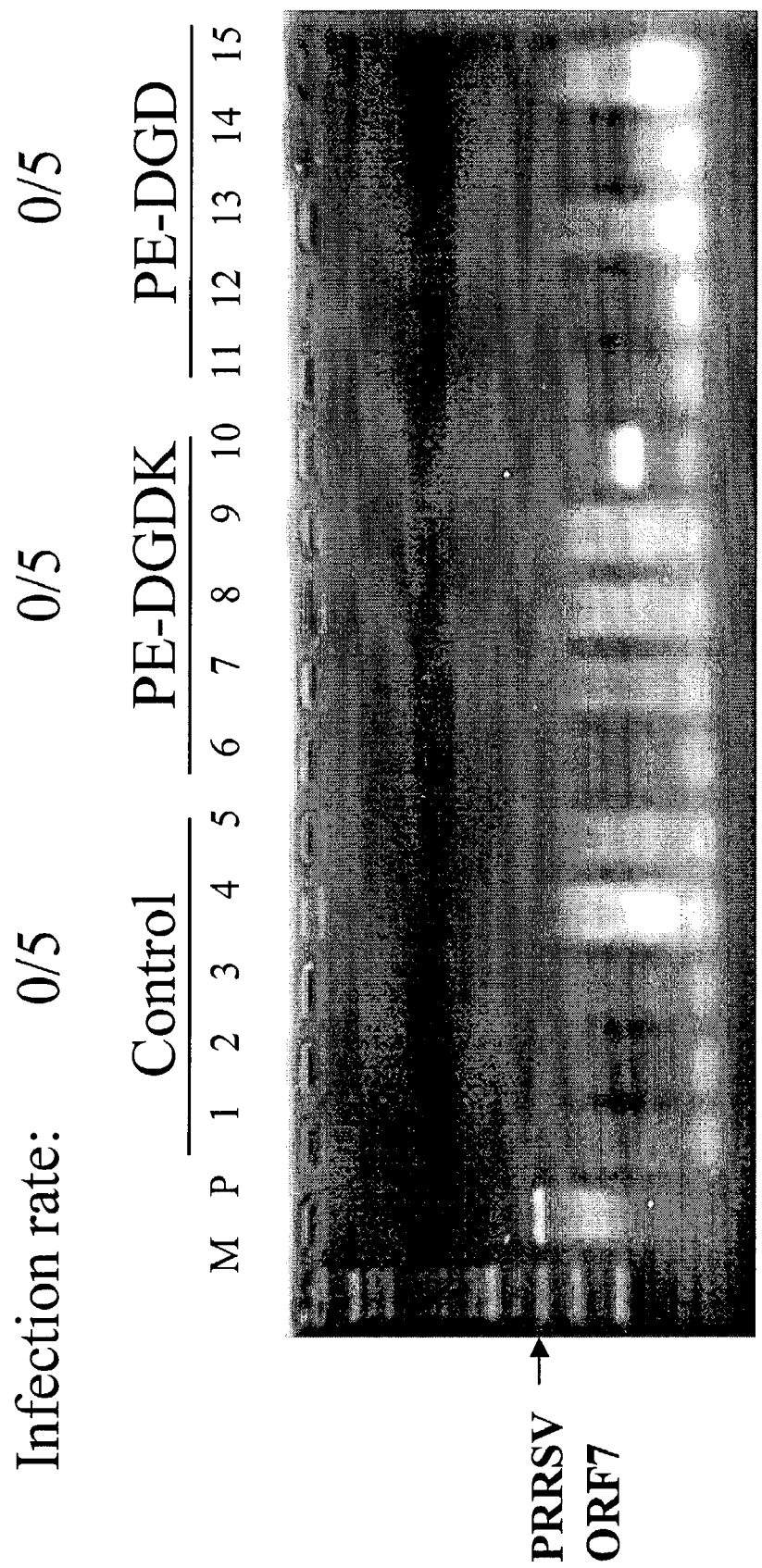
FIG. 12 illustrates the result of the detection of PRRSV by RT-PCR before a challenge of 15 piglets, wherein M represents the DNA marker and P represents the positive control.
Figure 13:
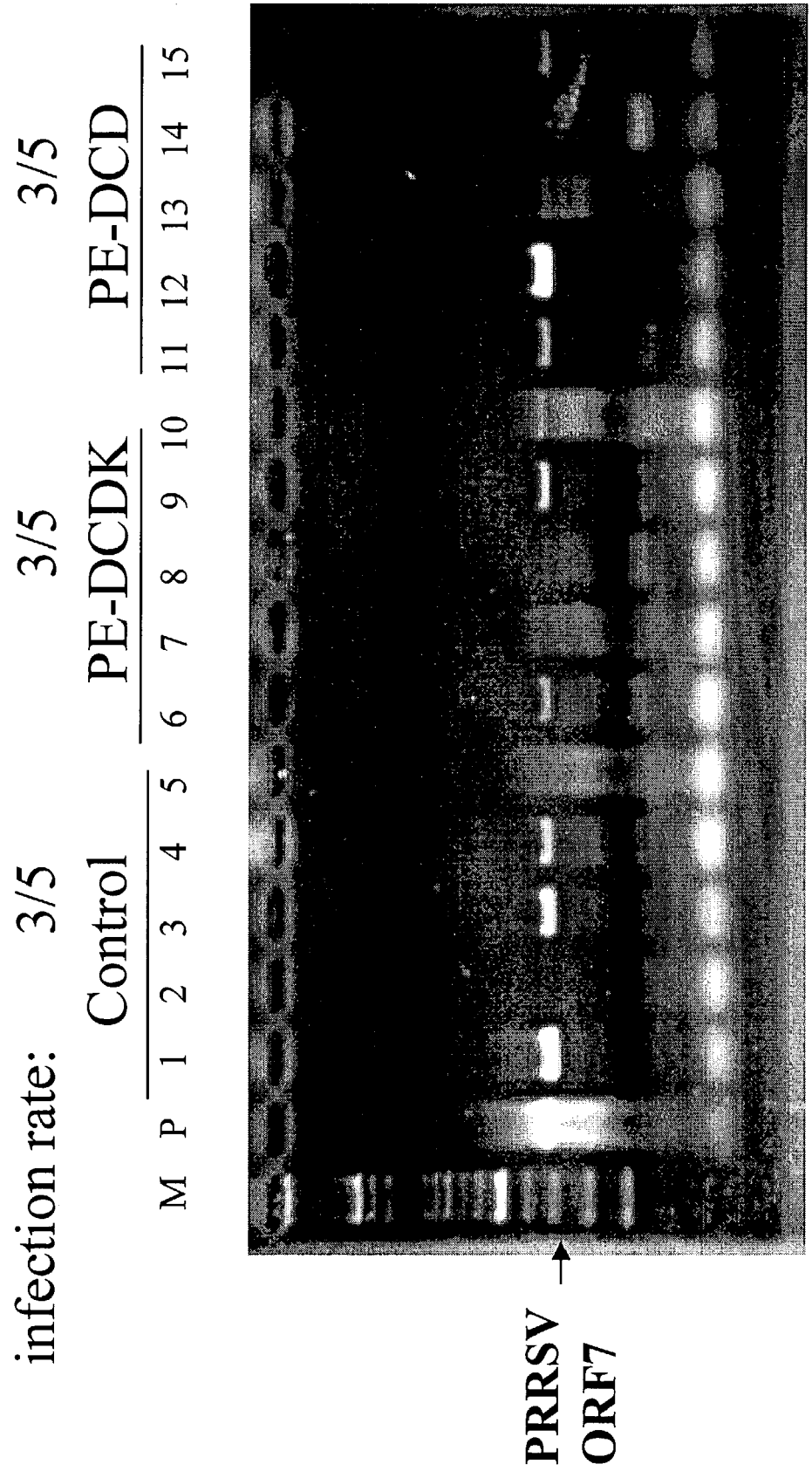
FIG. 13 illustrates the result of the detection of PRRSV by RT-PCR 3 days after the challenge of 15 piglets, wherein M represents the DNA marker and P represents the positive control.
Figure 14:
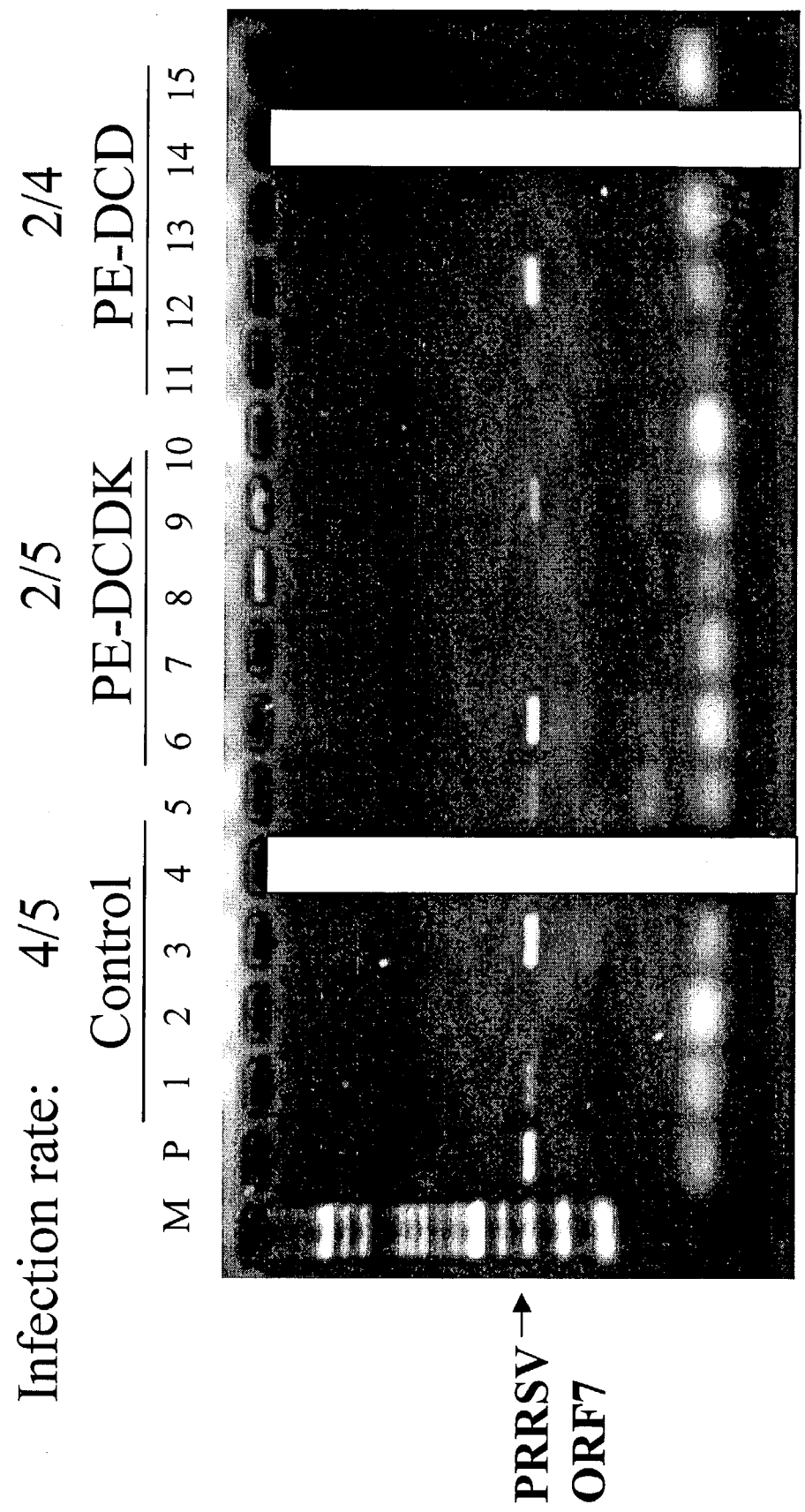
FIG. 14 illustrates the result of the detection of PRRSV by RT-PCR 7 days after the challenge of 15 piglets, wherein M represents the DNA marker and P represents the positive control.
Figure 15:
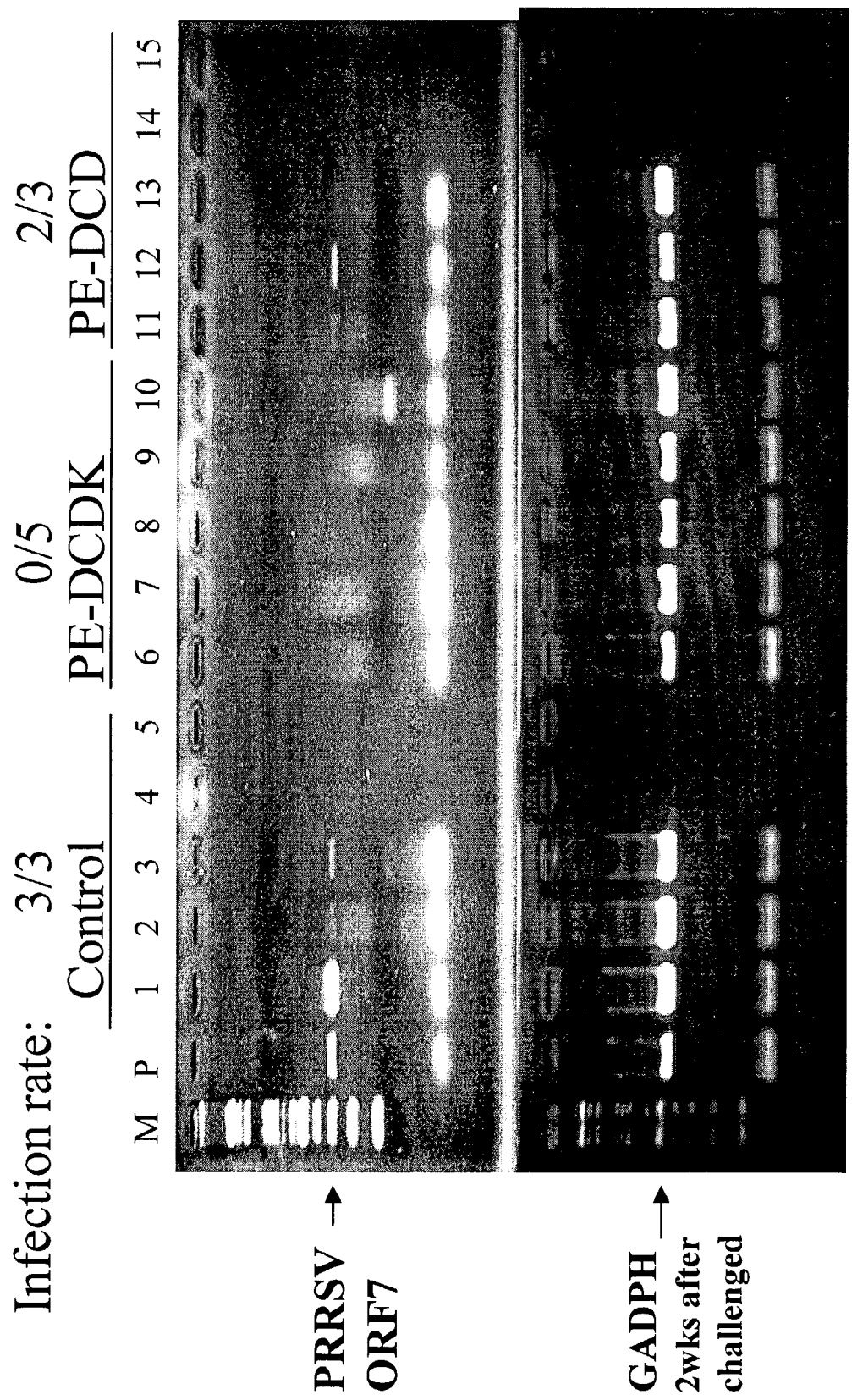
FIG. 15 illustrates the result of the detection of PRRSV by RT-PCR 14 days after the challenge of 15 piglets, wherein M represents the DNA marker and P represents the positive control.

The blood leukocyte samples of the piglets were assayed with RT-PCR for detecting PRRSV two weeks after the second immunization and the results are shown in FIG. 12. No viremia occurred in any of the piglets before the PRRSV challenge. The blood leukocyte samples of the piglets were again assayed with RT-PCR for detecting PRRSV after 3, 7, and 14 days after the challenge and the results are shown in FIGS. 13, 14 and 15, respectively.

The results are also summarized in Table 1:

TABLE 1

The PRRSV viremea ratio of piglets post-challenged with PRRSV

| Days | Control | PE-DGDk | PE-DGD |
|---|---|---|---|
| 3 | 3/5 | 3/5 | 3/5 |
| 7 | 3/4 (dead 1*) | 2/5 | 2/4 (dead 1*) |
| 14 | 3/3 (dead 2*) | 0/5 | 2/3 (dead 2*) |

*dead animal all were PRRSV viremea previously detected by RT-PCR

Necropsy was performed on all animals that had died and on all survivors at the end of the 2-week study. Macroscopic examination revealed pleuropneumonia in the lungs of five of the control pigs, four of the pigs in PE-DGD vaccinated, and two of the pigs in PE-DGDK group. More extensive lesions were observed in the control and PE-DGD vaccinated but not in PE-DGDK vaccinated group. It showed that the PRRSV ORF 7 fusion protein PE-DGDK can protect pigs from infection.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A fusion antigen specific for a target cell comprising:
an antigenic moiety;
a ligand moiety which is capable of reacting, recognizing or binding to a receptor on the target cell;
a *Pseudomonas* exotoxin A translocation domain II; and
a carboxyl terminal moiety comprising SEQ ID NO: 10.

2. The fusion antigen according to claim 1, wherein the target cell is an antigen presenting cell.

3. The fusion antigen according to claim 1, wherein the target cell is selected from the group consisting of T-cells, B-cells, dendritic cells, monocytes, and macrophages.

4. The fusion antigen according to claim 1, wherein the antigenic moiety is derived from porcine reproductive and respiratory syndrome virus, Circovirus type II, or human immunodeficiency virus.

5. The fusion antigen according to claim 1, wherein the antigenic moiety is porcine reproductive and respiratory syndrome virus (PRRSV) ORF 7.

6. The fusion antigen according to claim 1, wherein the antigenic moiety comprises at least one antigenic unit to which an adjacent antigenic unit is connected by a bridge region.

7. The fusion antigen according to claim 1, wherein the receptor to be bound to the ligand moiety is selected from the group consisting of antibody receptors, growth factor receptors, lymphokine receptors, cytokine receptors, and hormone receptors.

8. The fusion antigen according to claim 1, wherein the receptor to be bound to the ligand moiety is selected from the group consisting of TGFα receptors, IL2 receptors, IL4 receptors, IL6 receptors, IGF 1 receptors, CD4 receptors, IL 18 receptors, IL 12 receptors, EGF receptors, LDL receptors and α2-macroglobulin receptors.

9. The fusion antigen according to claim 1, wherein the ligand moiety is a *Pseudomonas* exotoxin A binding domain I.

10. A pharmaceutical composition comprising the fusion antigen according to claim 1 together with a pharmaceutically acceptable carrier.

11. A method of inducing an immune response in an animal comprising the steps of:
(a) providing a fusion antigen according to claim 1; and
(b) inoculating the fusion antigen into the animal,
wherein the immune response is directed against the pathogen from which the antigenic moiety is derived.

12. The method according to claim 11, wherein the target cell is an antigen presenting cell.

13. The method according to claim 11, wherein the antigenic moiety is derived from porcine reproductive and respiratory syndrome virus, Circovirus type II, or human immunodeficiency virus.

14. The method according to claim 11, wherein the antigenic moiety is porcine reproductive and respiratory syndrome virus (PRRSV) ORF 7.

15. The method according to claim 11, wherein the antigenic moiety comprises at least one antigenic unit to which an adjacent antigenic unit is connected by a bridge region.

16. The method according to claim 11, wherein the ligand moiety is a *Pseudomonas* exotoxin A binding domain I.

17. The method according to claim 11, wherein the receptor to be bound to the ligand moiety is selected from the group consisting of antibody receptors, growth factor receptors, lymphokine receptors, cytokine receptors, and hormone receptors.

18. The method according to claim 11, wherein the receptor to be bound to the ligand moiety is selected from the group consisting of TGFα receptors, IL2 receptors, IL4 receptors, IL6 receptors, IGF 1 receptors, CD4 receptors, IL 18 receptors, IL 12 receptors, EGF receptors, LDL receptors and α2-macroglobulin receptors.

19. The method according to claim 11, wherein the target cell is selected from the group consisting of T cell, B cell, dendritic cell, monocyte, and macrophage.

20. A fusion porcine reproductive and respiratory syndrome virus (PRRSV) ORF 7 antigen comprising
a PRRSV ORF 7 moiety;
a *Pseudomonas* exotoxin A binding domain I;
a *Pseudomonas* exotoxin A translocation domain II; and
a carboxyl terminal moiety comprising SEQ ID NO: 10.

21. A pharmaceutical composition comprising the fusion antigen according to claim 20 together with a pharmaceutically acceptable carrier.

22. A method of inducing an immune response in an animal against porcine reproductive and respiratory syndrome virus (PRRSV), which comprises the steps of:
(a) providing a fusion antigen according to claim 20; and
(b) inoculating the fusion antigen into the animal.

* * * * *

SEQUENCE LISTING

<160> NUMBER OF SEQ ID NOS: 11

<210> SEQ ID NO 1
<211> LENGTH: 388
<212> TYPE: DNA
<213> ORGANISM: Porcine reproductive and respiratory syndrome virus
<300> PUBLICATION INFORMATION:
<308> DATABASE ACCESSION NUMBER: Genbank/AF035409
<309> DATABASE ENTRY DATE: 1998-12-29
<313> RELEVANT RESIDUES: (2898)..(3269)

<400> SEQUENCE: 1

```
catatgccaa ataacaacgg caagcagcag aagaaaaaga aggggggacgg ccagccagtc      60 aatcagctgt gccaaatgct gggtaagatc atcgcccagc aaagtcagtc cagagttaag     120
ggaccgggaa ggaaaaataa gaagaaaaac ccggagaagc cccatttttcc tctggcgact     180 gaagatgacg tcagacacca ctttaccccc agtgagcggc aattgtgttt gtcgtcaatc     240
cagactgcct ttaatcaagg cgctggaact tgcatcctgt cagattctgg gaggataagt     300
tacactgtgg agtttagttt gcctacgcat catactgtgc gcctgatccg cgttacagca     360
ccaccctcag cataatgggc tggaattc                                        388
```

<210> SEQ ID NO 2
<211> LENGTH: 26
<212> TYPE: DNA
<213> ORGANISM: ARTIFICIAL
<220> FEATURE:
<223> OTHER INFORMATION: a forward primer for synthesizing PRRSV ORF 7

<400> SEQUENCE: 2

```
gtcacatatg ccaaataaca acggca                                           26
```

<210> SEQ ID NO 3
<211> LENGTH: 24
<212> TYPE: DNA
<213> ORGANISM: ARTIFICIAL
<220> FEATURE:
<223> OTHER INFORMATION: a forward primer for synthesizing PRRSV ORF 7

<400> SEQUENCE: 3

```
aagaattcca gctcatccat gctg                                             24
```

<210> SEQ ID NO 4
<211> LENGTH: 13
<212> TYPE: PRT

```
<213> ORGANISM: ARTIFICIAL
<220> FEATURE:
<223> OTHER INFORMATION: a carboxyl terminal moiety sequence in Example
      1

<400> SEQUENCE: 4

Lys Lys Asp Glu Leu Arg Asp Glu Leu Lys Asp Glu Leu
1               5                   10

<210> SEQ ID NO 5
<211> LENGTH: 39
<212> TYPE: DNA
<213> ORGANISM: ARTIFICIAL
<220> FEATURE:
<223> OTHER INFORMATION: a gene encoding the carboxyl terminal moiety in
      Example 1

<400> SEQUENCE: 5
aaaaaagacg aactgagaga tgaactgaaa gacgaactg                                 39

<210> SEQ ID NO 6
<211> LENGTH: 51
<212> TYPE: DNA
<213> ORGANISM: ARTIFICIAL
<220> FEATURE:
<223> OTHER INFORMATION: a reversed primer for generating the first
      polymerase chain reaction in Example 1

<400> SEQUENCE: 6
ttcatctctc agttcgtctt ttttgaggta gtcgacggag ctcgaattcg g                   51

<210> SEQ ID NO 7
<211> LENGTH: 52
<212> TYPE: DNA
<213> ORGANISM: ARTIFICIAL
<220> FEATURE:
<223> OTHER INFORMATION: a reversed primer for generating the second
      polymerase chain reaction in Example 1

<400> SEQUENCE: 7
agaattcctc gagtcattac agttcgtctt tcagttcatc tctcagttcg tc                  52

<210> SEQ ID NO 8
<211> LENGTH: 21
<212> TYPE: DNA
<213> ORGANISM: ARTIFICIAL
<220> FEATURE:
<223> OTHER INFORMATION: a forward primer for RT-PCR detection of PRRSV

<400> SEQUENCE: 8
ccagccagtc aatcagctgt g                                                   21

<210> SEQ ID NO 9
<211> LENGTH: 15
<212> TYPE: DNA
<213> ORGANISM: ARTIFICIAL
<220> FEATURE:
<223> OTHER INFORMATION: a reversed primer for RT-PCR detection PRRSV

<400> SEQUENCE: 9
gcggatcagg cgcac                                                          15

<210> SEQ ID NO 10
<211> LENGTH: 12
<212> TYPE: PRT
<213> ORGANISM: ARTIFICIAL
<220> FEATURE:
```

-continued

```
<223> OTHER INFORMATION: carboxyl terminal moiety of preferred fusion
      antigen

<400> SEQUENCE: 12

Lys Lys Asp Leu Arg Asp Glu Leu Lys Asp
 1               5                  10

Glu Leu

<210> SEQ ID NO 11
<211> LENGTH: 4
<212> TYPE: PRT
<213> ORGANISM: ARTIFICIAL
<220> FEATURE:
<223> OTHER INFORMATION: carboxyl terminal moiety of preferred fusion
      antigen

<400> SEQUENCE: 4

Lys Asp Glu Leu
```